United States Patent [19]

Gelder

[11] 4,315,906

[45] Feb. 16, 1982

[54] COLD INSOLUBLE GLOBULIN, ITS PURIFICATION AND USE

[75] Inventor: Frank B. Gelder, Shreveport, La.

[73] Assignee: New England Nuclear Corporation, Boston, Mass.

[21] Appl. No.: 40,995

[22] Filed: May 21, 1979

[51] Int. Cl.³ .................... A61K 49/00; A61K 43/00; C07G 7/00

[52] U.S. Cl. .................... 424/1; 260/112 R; 260/112 B; 424/1.5; 424/9

[58] Field of Search .................... 424/1.5, 1, 12, 9; 260/112 R, 112 B

[56] References Cited

U.S. PATENT DOCUMENTS 4,198,335  4/1980  Collen .................... 424/12

OTHER PUBLICATIONS

Saba et al., Surg. Annu., 7, 71-102, (1975).
Blumenstock et al., J. Biol. Chem., 253, 4287-4291, (1978).
Chen et al., Analyt. Biochem., 79, 144-151, (1977).
Kaplan et al., J. Reticuloendothel Soc., 15, 68a, (1974).
Kaplan et al., J. Reticuloendothel Soc., 20, 375-383, (1976).
Kishore et al., First Int. Symp. on Radiopharm. Chem., Sep. 21-24, 1976.

*Primary Examiner*—Christine M. Nucker
*Attorney, Agent, or Firm*—Sewall P. Bronstein; George W. Neuner

[57] ABSTRACT

A highly purified, biologically active cold insoluble globulin (CIG) preparation is provided having specific opsonic activity of at least 1000 units per mg of CIG. Methods of purifying CIG using affinity antibody columns are described in which the biological activity of the purified CIG is greater than 95% of the activity of the starting material.

The purified CIG can be radiolabelled and radiopharmaceutical preparations containing such CIG are useful as scanning agents for in vivo localizing of areas where CIG-binding determinants are expressed. Such areas include thrombi and damaged tissue such as burns, heart, liver, spleen, muscle, skin, kidney and the like. These areas of localized radiolabelled CIG can be visualized with a gamma camera.

36 Claims, No Drawings

COLD INSOLUBLE GLOBULIN, ITS PURIFICATION AND USE

FIELD OF THE INVENTION

The present invention relates to cold insoluble globulin (CIG), methods for purifying CIG, and methods for using in vivo radiopharmaceuticals of CIG as agents for localizing sites of trauma in a higher animal.

BACKGROUND OF THE INVENTION

Cold insoluble globulin (CIG) is a plasma protein that coprecipitates with fibrinogen and other proteins found in the cryoprecipitate of plasma and related fractions. It appears that CIG has been reported in the literature under a variety of names including, for instance, $\alpha_2$-glycoprotein, non-immune $\alpha_2$-opsonic macroglobulin, fibronectin or plasma fibronectin, human plasma cryoprecipitate, humoral recognition factor, antigelatin factor, CIg, LETS protein, $\alpha_2$-surface binding macroglobulin.

It has been suggested that CIG possesses opsonic activity. Opsonins are serum factors that promote the phagocytosis of foreign particulate matter.

Phagocytosis is the specialized function of certain cells in higher organisms involved in host defense with the purpose of ingesting and digesting harmful particles such as bacteria, antigen-antibody complexes, tissue debris and colloidal pollutants. This process depends on humoral recognition factors (opsonizing factors) which give it selectively and efficiency (DiLuzio et al., *Advan. Exp. Med. Biol.* 15, 373–390 (1971)).

The reticuloendothelial system (RES) is involved in the phagocytic clearance and subsequent intracellular degradation of both blood-borne foreign and endogenous effecte, particulate, or denatured matter. This vascular clearance capacity of the RES is primarily mediated by sessile phagocytic cells which line the vascular compartment in the linear, spleen, lung, and bone marrow. The reticuloendothelial system is a defense mechanism which when operating efficiently allows higher animal forms to survive severe stress such as trauma, sepsis, surgery, etc. Reticuloendothelial cells are found, for example, fixed in the liver, spleen, bone marrow and lymph nodes as well as circulating in the vascular tree and tissue spaces. The major portion of the RES consists of sessile macrophages. Due to their strategic anatomic locations and intense phagocytic activity they filter the blood system to protect the pulmonary and systemic vascular beds from microembolism and trauma caused by accumulation of such products. As a clearance mechanism, they remove from the blood bacteria, denatured proteins, immune complexes, microaggregates of fibrin, injured platelets, viruses, tumor cells, endotoxins, lysosomal enzymes, other toxic and/or antigen bloodborne particulate matter, and the like.

Through their opsonic activity, a variety of proteins have been shown to possess the ability to promote the phagocytic activity of the reticuloendothelial cells. These proteins include several $\alpha_2$-opsonic glycoproteins, antibodies, opsonically active fragments of the complement system and C-reactive protein. There are distinct differences among these proteins with regard to chemical characterization and substrate specificity. One of the $\alpha_2$-opsonic glycoproteins, plasma fibronectin, has been considered to be a non-specific thermolabile factor involved in mononuclear phagocytosis of foreign colloids, denatured protein, leukemic leukocytes and certain tumor cells, with minimal documented importance in bacterial phagocytosis. By contrast, antibodies or immunoglobulins, certain components of the complement system and C-reactive protein are considered to be specific and are actively involved in the opsonic mediated phagocytosis by both mononuclear and polymorphonuclear leukocytes. As stated by Molnar et al, *Biochem. Biophys. Acta*, 493, 37–54 (1977), the best studied opsonins are antibodies and certain complement components.

Molnar et al., supra, suggested that in the rat, nonspecific opsonin could be involved as a first line of defense against invading microorganisms in a non-specific manner. This mechanism has been proposed to be essential for survival until the immune system takes over. According to Blumenstock et al., *J. Reticuloendothel Soc.*, 19, 157–172 (1978), non-specific stimulation of the RES results in a state of hyperphagocytosis that can be quantified by blood clearance of test colloids. This hyperphagocytosis has been correlated with increased resistance to infection, malignant disease and traumatic shock. Experimental induction of RES phagocytic depression caused by colloid induced blockage decreases the resistance to such insults. Following burn shock or traumatic injury, the consumptive depletion of both specific and non-specific opsonic proteins appears to predispose higher animals to septicemia and/or microvascular collapse, i.e., shock.

Studies have indicated that the function of the reticuloendothelial system is related to survival after severe trauma and shock. Thus, a reduced RE function has resulted in a markedly depressed tolerance to trauma in animals while an enhanced tolerance to trauma has been found in animals with RES hyperactivity.

Van Oss et al., *Immunol. Commun.*, 3, 329–335 (1974) found that $\alpha_2$-glycoprotein ($\alpha_2$HS glycoprotein) was decreased to 25 to 50% of normal values in each of eight trauma patients studied. This glycoprotein appeared to act directly on the surface of microorganisms and they considered it a true aspecific opsonin. They felt that the decreased concentration of this protein in trauma patients was a likely factor contributing to the decreased resistance to bacterial infections. They also noted another factor, an $\alpha_1$ acid glycoprotein, which may be an inhibitor of phagocytosis.

Scoville et al., *J. Trauma*, 16, 898–904 (1976) reported on 20 consecutive patients with multiple injuries from motor car accidents or blunt trauma, each of whom had a documented episode of hypotension. Plasma opsonic activity (detected using a liver in vitro bioassay) was decreased markedly following trauma. The initial post-traumatic hypoopsonemia was more severe in the non-surviving patients than in the surviving patients. Survivors, following trauma, manifested restoration of opsonin levels with a definite transient rebound hyperopsonemia during the recovery phase. Non-surviving patients exhibited persistant systemic $\alpha_2$-globulin opsonic deficiency. They concluded their report with the following statement, "the importance of posttrauma RES dysfunction to survival following severe injury warrants further investigation and clinical consideration".

Surgery has induced alterations in plasma fibronectin concentrations. DiLuzio and Lindsey, *Proc. Soc. Exp. Biol. Med.*, 143, 715–718 (1973) evaluated the influence of surgical stress plasma opsonin levels in both renal transplant donors and recipients by the in vitro liver slice bioassay. Both surgical populations showed significant depletion of opsonin activity at 1–7 days post-surgery. Restoration occurred in all cases.

Saba and Scovill, *Surg. Annu.*, 7, 71–102 (1975) reported that following surgical intervention there was a transient but profound depression in RE phagocytosis mediated by a deficiency in circulating plasma opsonic capacity. Eventual restoration of RE function during the later post-operative period could be correlated with a recovery of the blood opsonic levels. Following major accidental or surgical trauma a failure in systemic RE phagocytosis was observed. These authors suggest that this occurrence may be significant to host defense against septicemia. For a transient period of the post injury interval, this failure may increase the susceptibility of the host to pulmonary microvascular localization of denatured protein such as fibrin as well as to embolization of fat globules and blood-borne tumor cells. They concluded that with the isolation of the humoral factor (opsonic protein), this tool would have both diagnostic as well as prognostic value as an humoral index of the functional state of the RES. Such values would be helpful prior to and following surgery or during the course of clinical therapy for malignancy and traumatic shock.

Aronsen et al., *Scand. J. Clin. Lab. Invest.* 29, suppl. 124: 127–136 (1972) measured cold insoluble globulin (CIG) in plasma following cholecystectomy. CIG showed an initial rapid but small drop in concentration followed by a slow increase with a concentration maximum by one week post-operation and then a fall to normal. An electroimmuno precipitation assay was used to determine the concentrations with the mean determined as a percentage of that found for normals. The pre-operative mean value was 96% with a standard deviation (S.D.) of 22 and a range of 58 to 135. However, the mean at post-operative day 2 was 79% with a S.D. of 23 and a range of 35 to 120.

Kaplan and Saba, *J. Reticuloendothel Soc.*, 15, 682 (1974) found a 76% decrease in opsonin levels and an associated RE depression 60 minutes post-surgery (celiotomy) in rats. Purified $^{125}I$ labeled opsonin protein was found to localize at the incision site.

Kaplan et al., (1976) suggested that the accumulation of opsonic protein at the site of surgery was the result of affinity for damaged tissue. They also noticed a shorter biological halflife for opsonic protein in operated animals than found in normal rats (134 minutes in normals). They concluded that the relationship between the level of circulating opsonic protein and the post-operative RES defense in terms of non-specific clearance of microaggregates and foreign abnormal cells from the blood warrants investigation.

Molnar et al., supra (1977) labeled membrane fragments from homogenized tissues and showed that these fragments were taken up by liver slices. This uptake was dependent on the concentration of the rat $\alpha$-2-opsonin.

CIG was first partially purified in a biologically active form by Mosesson and Umfleet, *J. Biol. Chem.*, 245, 5728–5736 (1970). They suggested in this report that the CIG (plasma fibronectin) level in serum is somewhat lower than that in plasma due to incorporation in the fibrin clot. An improved method for purifying CIG is reported by Chen et al., *Analyt. Chem.*, 79 144–151 (1977).

Mosher, *J. Biol. Chem.*, 250, 6614–6621 (1975), based on in vitro data, suggests that in the presence of activated plasma factor XIIIa (fibrin stabilizing factor) CIG can be covalently cross-linked to fibrin alpha chain or to other CIG molecules. Mosher, *J. Biol. Chem.*, 251, 1639–1645 (1976) suggested that a clot formed from normal plasma would contain 94% fibrin and 6% CIG assuming 50% of the CIG is cross-linked to fibrin. Mosher, *Thromb. Res.*, 9, 37–45 (1976) further reported decreased levels of CIG in monkeys that developed disseminated intravascular coagulation following infection with Rocky Mountain spotted fever. Mosesson et al., supra (1975) reported that some of his unpublished work suggests that CIG levels tended to be reduced in a significant proportion of patients manifesting the disseminated intravascular coagulation syndrom.

Recently, Blumenstock et al, *J. Biol. Chem.*, 253, 4287–4291 (1978) suggested that human CIG (or plasma fibronectin) showed immunological identity with their human opsonin preparations. Although recognizing the fact that proof of biological identity would require a demonstration that highly purified CIG is opsonically active, no evidence could be obtained because isolation of CIG by ethanol fractionation (as reported by Mosesson et al., *Biochem. Biophy. Acta*, 386, 509–524 (1975)) yielded an inactive product.

Thus, it can be seen that a biologically active, highly purified CIG is desireable to characterize its opsonic activity and to aid in quantifying opsonic levels in the blood for diagnostic and therapeutic purposes.

SUMMARY OF THE INVENTION

The present invention provides a purified, biologically active cold insoluble globulin preparation having specific opsonic activity of at least 1000 units per mg of CIG, methods for purifying CIG to obtain such high specific activity, and methods for using radiolabelled CIG for localizing biological matter comprising CIG-binding determinants (defined hereinafter), for example, thrombi and areas of damaged tissue due to infarct, large vessel thrombosis, abscess, ulcer, burn, and the like.

The method of purifying CIG in accord with the present invention comprises preparing CIG antisera (anti-CIG), immobilizing the anti-CIG on a support matrix, applying a crude CIG preparation to the anti-CIG support matrix to bind the CIG, and eluting purified CIG. Purified CIG preparations containing at least 95% of the opsonic activity contained in the starting material have been obtained. CIG preparations having a specific activity more than 30 times that achieved using prior techniques have been obtained using the methods in accord with my invention.

Although not wishing to be bound by any theory, my recent studies suggest that CIG functions as a recognition mechanism to distinguish, for instance, damaged tissue from normal tissue. There is a determinant or group of determents (herinafter referred to as "XCIG-binding determinants") expressed on the surface of damaged tissue which are sequestered or unavailable in normal tissue. Following injury or cell death, these CIG-binding determinants are expressed and available for CIG attachment. Upon attachment to, for instance, damaged tissues, chemotactic factors are liberated and phagocytic cells move to the site of injury and remove damaged cells and cell debris.

CIG will recognize or bind to any protein or cellular constituent containing these specific CIG-binding determinants. Two proteins have been identified as containing these specific CIG-binding determinants. One is a collagen, both native and denatured, and the other is fibrin crosslinked by fibrin stabilizing factor (FST). Biological matter containing CIG-binding determinants include thrombi; certain tumors; damaged heart, liver, spleen, muscle, skin, kidney, and connective tissues; and the like.

CIG can be labelled with a suitable radionuclide, for instance, with $^{125}$I, $^{131}$I, 99mTc, etc. and used as an imaging agent to localize various sites of expressed CIG-binding determinants, for example, damaged tissue in the body such as abscess, burns, ulcer, infarct, large vessel thrombosis, tumors, transplants undergoing rejection, and the like. The highly purified CIG in accord with my invention, when radiolabelled with, for instance, $^{125}$I has been found to provide a target to non-target (background) ratio of at least 10 to 1 which makes it useful when labeled with a suitable radionuclide as a as an imaging agent for localizing damaged tissue and the like as described above. A 10 to 1 ratio over background is generally considered to be the lower threshold for practical use as an imaging agent.

DETAILED DESCRIPTION OF THE INVENTION

In accord with the present invention a highly purified, biologically active CIG preparation having a specific opsonic activity at least 1000 units per mg. of CIG, and preferably at least 2000 units per mg. of CIG is provided.

As used herein, one "unit" of opsonic activity is defined as that amount of material which causes the uptake of 1% of a standardized total dose of radioactive particles added to the liver tissue in the rat liver slice bioassay for phagocytic uptake of radiolabelled particles using the materials and procedures described in Examples 4 and 5.

Sources of CIG include, for example, serum, plasma, fractions of serum or plasma such as Factor VIII preparations and byproducts of Factor XIIIa purification, and supernatents from appropriate tissue culture cell lines.

CIG can be purified to obtain the above specific activity by affinity chromatography on an anti-CIG column. First, to prepare anti-CIG, CIG is partially purified using the method described by Molnar, et al, *Biochem. Biophys. Acta*, 493, 37–54 (1977) A host animal such as a rabbit is immunized with partially purified CIG to produce antisera to the CIG (anti-CIG). The anti-CIG is adsorbed with CIG-negative plasma to remove contaminating antibody specificities. The anti-CIG is then isolated and immobilized on a support matrix, for example, by covalently coupling to a substrate such as Sepharose ® 4B. This product is ready for use in the affinity chromatography purification of CIG. Using this procedure, CIG having a specific opsonic activity of more than 2000 units per mg. of protein have been obtained.

A high purity CIG can also be obtained as a by-product of the large scale purification of fibrin stabilizing factor (FSF, blood coagulation factor XIIIa) using the method described by Lorand et al, *Methods Enzymol.*, 19, 770–782 (1970). I have found that CIG separates from FSF in the DEAE cellulose chromatography step employed in the procedure of Lorand et al and the CIG can be eluted in a salt gradient at a concentration of about 0.15 M NaCl at pH 7.5. The CIG pool collected can be concentrated by precipitation by ammonium sulfate at about 40% saturation.

I have found that CIG localizes at the site of protein or cellular components expressing CIG-binding determinants, for instance, thrombi and damaged tissue, for example, burn injury, myocardial infarct, tumor, and the like. By radiolabelling CIG with, for instance, $^{125}$I by the Chloramine-T method and injecting it, either intravenously or intralymphatically depending upon the particular area being scanned, into host animals, e.g. rats with burn injury, tumor, etc. the concentration of radiolabelled CIG increases in damaged tissues even without as significant blood pooling or vascular fluid shift as would be expected with surgical trauma. The amount of radionuclide used in labelling depends upon the particular radionuclide being used and the proposed target. Labelling with as little as one atom of radionuclide per 100 molecules of CIG, or less up to ratios of radionuclide per molecule of CIG preceding those ratios which inactivate the CIG can be useful. Preferably the radiolabelled CIG contains at least 1 radioactive atom per ten molecules of CIG and more preferably at least 1 atom per molecule.

It is believed that the specificity of CIG for CIG-binding determinants causes the labelled CIG to bind to damaged tissue thus causing localization of radioactivity.

Radiopharmaceutical preparations in accord with my invention contain radiolabelled CIG, in a pharmaceutically acceptable carrier. Radio-iodination has been found to be quite satisfactory for labelling CIG for use in accord with this invention. The CIG is provided in the preparation in a concentration in the range of from about 0.1 mg/ml to about 10 mg/ml, preferably from about 0.5 mg/ml to about 2.0 mg/ml. Any suitable pharmaceutically acceptable carrier may be used. For example 5% serum albumin of the species under investigation in a physiological buffer has been found to be satisfactory.

The radiopharmaceutical preparation of this invention can be injected intravenously or lymphatically into higher animals depending upon the particular sites being visualized. The amount of radiolabelled CIG injected depends upon the biological activity and the amount of labelling. The amount of injected CIG can be determined by those skilled in the art depending upon various known considerations including, for example, the particular radionuclide used for labelling, the target tissue, the rate of clearance from the blood or lymphatic system, clearance from the most sensitive tissues, whole body clearance, etc. The acceptable ranges for administration of radiolabelled materials for various procedures are tabulated, for instance, in the Physicians Desk Reference for Nuclear Medicine published by Medical Economics Co.

The radiopharmaceutical preparations of this invention, when injected into rats, have provided radioactivity concentrations at areas of damaged tissue that are ten or more times the background. Concentrations even as high as fifty times background have been achieved in localization at such tissue areas. A target to non-target ratio of at least 10 to 1 as thus achieved enables the use of radiolabelled CIG to be a practical tool in localizing sites of thrombi and damaged tissue. The areas expressing CIG-binding determinants can then be visualized using radioscintigraphic imaging equipment.

The advantage of having a radiolabelled material that localizes specifically in areas of damaged tissue will be readily appreciated by those skilled in the art. For instance, myocardial infarct is presently localized by radiolabelled pyrophosphate; however, pyrophosphate also localizes in bone, and thus the infarct must be distinguished from the thoracic cage which also appears on the film.

For short half-life radionuclide such as technetium-99 m and iodine-123 that are frequently employed by the user in the field, supplying CIG in appropriate kit form would be advantageous.

Other advantages of the materials and methods of this invention will be apparent to those skilled in the art upon consideration of the following examples which are provided to further aid in the understanding and practice of my invention.

EXAMPLE 1

Preparation of Anti-CIG

White New Zealand rabbits were immunized with rat, human or dog CIG purified by the method described by Molnar et al, *Biochem. Biophys. Acta*, 493 37–54 (1977). These preparations still remained contaminated with other serum proteins. The CIGs (1 mg protein/ml) were emulsified with an equal volume of complete Freunds adjuvant and injected intramuscularly on day 0, 14, 21, 28 and 35. Animals were exsanguinated seven days after the last injection. Sera were heat inactivated at 56° C. for 30 min. and assayed for immunoreactivity. Antisera from each of the three species demonstrated one major band and two minor bands after immunodiffusion against respective normal sera. Antisera were adsorbed with the appropriated CIG depleted normal rat, human and dog sera covalently coupled to Sepharose ® 4B, CIG having been depleted from these sera by exposure to gelatin-latex particles. Following adsorption, these antisera demonstrated a single precipitation band against their respective sera. Adsorbed antisera (anti-CIG) were precipitated with ammonium sulfate at 40% saturation, dissolved and dialized against 10 mM phosphate buffer pH 7.0 and chromatographed on DE-52 (a diethylaminoethyl cellulose available from Whatman) equilibrated with the same buffer. The protein eluting with 10 mM phosphate buffer, pH 7.0, contained most of the antibody activity. The final products were stored at 4° C. in phosphate buffered saline with 0.1% sodium azide until used.

Subsequent antisera were raised to antibody affinity purified opsonin using the same immunization schedule as before. These antisera were demonstrated to be monospecific for CIG without adsorption.

EXAMPLE 2

Preparation of the Antibody Affinity Chromatography Column

The anti-CIG from Example 1 was covalently coupled to Sepharose ® 4B by the cyanogen bromide reaction (10 mg protein per gram wet resin). An affinity chromatography column was prepared by loading the Sepharose ® 4B-anti-CIG into a column.

The Sepharose ® 4B-anti-CIG column (0.9×5 cm) was equilibrated with phosphate buffered saline (0.01 M phosphate, 0.85% NaCl, pH 7.3) at room temperature and 10–20 ml of fresh serum or plasma was applied and eluted with the same buffer until the absorbance at a wave length of 280 nm ($A280$) was less than 0.01. The CIG was eluted with 0.1 M glycine-HCl buffer, pH 2.3. The yield of CIG was almost quantitative and the purity was markedly superior to that obtained with reported previous purification techniques. No CIG was found in the flow through peak suggesting quantitative absorption to the column. The acid eluate contained purified CIG with no detectable contaminants.

EXAMPLE 3

Rocket Immunoelectrophoretic Quantitation of CIG

Rocket immunoelectrophoresis was carried out with 0.75% agarose in Gelman high-resolution buffer (pH 8.8, ionic strength 0.03, Gelman Instrument Co., Ann Arbor, Michigan). For analysis of immunoreactive CIG the agarose gel was mixed with a predetermined amount of anti-CIG at 56° C. and layered onto glass slides held in a Gelman Immunoframe to produce a uniform thickness of 2 mm. The optimal concentration of antiserum required in the assay was determined by evaluating the migration of CIG standards in gels containing varying concentrations of anti-CIG. The migration of seven CIG standards (400, 350, 300, 250, 200, 100 and 50 µg/ml) was evaluated. These standards were prepared from affinity-purified CIG (Example 2). The antiserum dilution that gave a crisp precipitation reaction with maximum migration was selected for the assay. With each quantitative assay a standard curve was prepared. Holes (3 mm in diameter and 8 mm apart) were cut out 15 mm from the end of each slide. Ten µl of test sera (undiluted and diluted 1:2) and dilutions of CIG standard used for calibration were pipetted into the walls. Electrophoresis was performed at 10 ma/frame for 10 hours. Rocket arc lengths were measured and a standard curve plotted. The distance traveled by the CIG was proportional to its concentration. Multiple test samples and standards evaluated on the same day and at weekly intervals showed a variation of less than 5% from the observed initial values.

EXAMPLE 4

Preparation of Gelatin Latex Particles

Two ml of carboxylated latex (0.4 µm or 0.2 µm beads, 10% dry weight; Dow Chemical Co., Indianapolis, Ind.) were mixed with 10 mg of gelatin (Nutritional Biochemicals Co., Cleveland, Ohio) in 1 ml of water and 500 µl of a solution containing 4 M sodium chloride and 0.8 M sodium borate (adjusted to pH 8 with hydrochloric acid) was added. Finally, 50 mg of N,N'-dicyclohexylcarbodiimide (Aldrich Chemical Co., Milwaukee, Wis.) in 0.5 ml of ethanol were added, and aliquots of the mixture were kept at ambient temperature for 3 hours, and at 4° C. overnight. Then 1 mg of tyrosine hydroxamide (Calbiochem, La Jolla. Cal.) was admixed, and the suspension was brought to ambient temperature for one hour, following which it was diluted to 40 ml with a solution (buffer A) containing 0.15 M sodium chloride and 10 mM sodium borate at pH 8. The latex particles were harvested by centrifugation at 15,000 rpm for 10 min. in a Sorvall RC 2B centrifuge, using an SS-34 rotor; they were washed with 40 ml of buffer A and collected again by centrifugation. This washing procedure was repeated twice, and the latex particles were finally suspended in 10 ml of buffer A. One mg of the above latex particles (dry weight) were determined to have bound about 28 µg of gelatin.

EXAMPLE 5

Radiolabelling Gelatin-Latex Particles

Two ml of the latex-bound gelatin suspension, prepared as described in Example 4 were mixed at room temperature with 0.1 ml of 20 mM sodium iodide, 100 µl (100 μLCi) of $^{125}$I sodium iodide (Amersham-Searle, Arlington Heights, Ill.), and 25 μl of Chloramine-T (1 mg/ml, Aldrich Chem. Co., Milwaukee, Wis.). Ten minutes later, another 25 μl of the Chloramine-T solution were added and the reaction was allowed to proceed for 10 minutes before 1 mg of sodium tetrathionate was admixed and the latex particles were removed by centrifugation (as in Example 4). The sediment was washed and centrifuged 7 times in succession, each time with 40 ml of buffer A containing 1 millimole of sodium iodide. Then, following dialysis against 2 changes of buffer A (each of 4 liter volume and lasting for about 12 hours), the radioactive particles were harvested by centrifugation, suspended in 10 ml of buffer A and stored at 4° C. The preparation contained less than 0.1% of non-sedimentable radioactivity (15,000 rpm, 10 min) and had a latex content of about 4 mg per ml of suspension. Immediately prior to use in phagocytic experiments, and aliquot of the suspension was diluted 10-fold into Krebs-Ringer-Phosphate buffer of pH 7.4 (Umbreit et al, *Manometric Techniques and Tissue Metabolism*, 5th Ed., p. 146, Burgess Publ. Co., Minneapolis, Minn. (1972) and dispersed by brief sonication (10 sec burst at setting 2; Model W140D, Brenson Sonifier Plainview, N.Y.).

EXAMPLE 6

Rat Liver Assay for Opsonic Activity

White male or female, Holtzmann of Sprague Dawley rats weighing 250-350 g were sacrificed by decapitation and, following exsanguination, 0.5-1 mm thick liver sections were prepared and cut into 100±30 mg (wet weight) pieces. Each slice was immersed in a Wheaton vial containing 10 units of heparin, test samples and other additions in Krebs-Ringer buffer (Example 5) with a total volume of 1.2 ml. The phagocytic process was initiated by the addition of 0.1 ml of the ten-fold diluted $^{125}$I-labelled gelatinized latex suspension of Example 5 (approximately 20,000 cpm). Samples were incubated at 37° C. for 30 minutes while the vials were shaken gently in a metabolic shaker (New Brunswick Instr., New Brunswick, N.J.). Following the phagocytic reaction, the tissue slices were placed in a tray containing 2 liters of cold 0.1 M sodium chloride and were rinsed to remove particles which were not bound by the liver. Each slice was then transferred into a counting tube for measurement of radioactivity (Model 1085 γ-counter, Nuclear Chicago, Chicago, Ill.). Experiments were performed in triplicate. Then, after correcting for background radiation, the uptake of radioactivity was calculated for 100 mg of tissue and was averaged for the 3 measurements. Results for the opsonin-dependent uptake of particles are tabulated in terms of the percentage of the total dose of latex-bound radioactivity originally added to the tissues, subtracting the percentage uptake determined similarly using Krebs-Ringer buffer in place of a test sample.

EXAMPLE 7

Prior Art Purification of CIG

CIG was purified rat serum and rat plasma by the method described by Molnar et al (1977), supra. Opsonic activity of the purified CIG was determined by the rat liver bioassay described in Example 6. The results are given below in Table 1.

TABLE 1

| | Protein mg/100 ml | | Total opsonin units* in 100 ml ($\times 10^{-3}$) | | Specific opsonin activity units/mg | |
|---|---|---|---|---|---|---|
| | Plasma | Serum | Plasma | Serum | Plasma | Serum |
| Starting material 0.35 sat. (NH$_4$)$_2$SO$_4$ | 7000 | 7000 | 100 | 36 | 14 | 5 |
| Fractions | 690 | 650 | 54 | 27 | 79 | 42 |

*Unit defined previously

EXAMPLE 8

Purification of CIG as a By-Product from Fibrin Stabilizing Factor Solution

CIG was prepared as a by-product of purifying the fibrin stabilizing factor (blood coagulation Factor XIIIa) from 10 liters of fresh or outdated human plasma according to the procedure described by Lorand et al. (1970), supra. Separation of Factor XIIIa from CIG was achieved by DEAE-cellulose chromatography using a linear sodium chloride gradient of 50 mM Tris-HCl buffer at pH 7.5, containing 1 mM of EDTA. While Factor XIIIa emerged at an ionic strength of about 0.09, the essentially pure CIG peak eluted at about 0.15. The latter (300 ml, 1 mg/ml protein) was concentrated by precipitation with a final concentration of 40% saturated ammonium sulfate. After centrifugation, it was dissolved in 60 ml of 0.05 M Tris-HCl buffer, pH 7.5, containing 1 mM EDTA and 0.1 ml of Trasylol (10,000 Kallikrein units/ml; FBS Pharmaceuticals, New York, N.Y.). In order to remove possible small molecular weight contaminants, gel filtration on Sepharose ® 6B (Pharmacia, Sweden; 2.5×110 cm column) was carried out in the above buffer using a protein load of 40 mg. All material absorbing at 280 nm (ISCO detector; Lincoln, Nebr.) emerged as a single peak an elution volume to void volume ratio of 1.2. This material was concentrated by precipitation with ammonium sulfate, taken up in the EDTA and Trasylol containing Tris buffer as before, and dialyzed against the same. Typically, about 400 mg of pure CIG were obtained from 10 liters of plasma and the preparation (8 mg protein/ml) was stored at 4° C.

EXAMPLE 9

Purification of CIG by Antibody Affinity Chromatography

Rat serum (17 ml) was applied to a 0.9×5 cm column of Sepharose ® 4B coupled to rabbit IgG against rat CIG as described in Example 2, and the column was washed further with 30 ml of Krebs-Ringer solution. Specifically adsorbed protein was eluted subsequently with 0.1 glycine-HCl (pH 2.3 neutralized immediately by the addition of K$_2$HPO$_4$ and dialyzed against Krebs-Ringer solution at 0° C., overnight. The opsonic activity of the purified rat CIG is tabulated below.

TABLE 2

| | Total Opsonizing Unit | Specific oponizing activity units/mg protein |
|---|---|---|
| Starting Serum (17 ml)* | 2040 | 1.7 |
| Serum effluent (17 ml)* | 0 | 0 |

TABLE 2-continued

| | Total Opsonizing Unit | Specific oponizing activity units/mg protein |
|---|---|---|
| Dialyzed glycine eluate (7 ml) | 4200 | 1300 |

*Aliquots were kept on ice and were tested for opsonizing activity together with the dialyzed glycine eluate.

Improvements in activity and stability can be obtained by eliminating plasmin activity and gradually neutralizing the final product.

EXAMPLE 10

Comparative Analysis of CIG Purifactions

The specifiic activity of CIG preparations obtained by various purification procedures was assayed in accord with the procedure of Example 6. The results are tabulated below.

TABLE 3

| Starting Material | Method of Purification | Specific Activity units/mg |
|---|---|---|
| Rat serum | Example 7 (prior art) | 42 |
| Rat plasma | Example 7 (prior art) | 79 |
| Rat serum | Example 2 | 2100 |
| Human serum | Example 2 | 2350 |
| Human plasma | Example 8 | 2650 |

EXAMPLE 11

Preparation of Radiolabelled CIG

A solution containing 1 mg CIG and 17.5 millicuries $^{125}I$ in 1 milliliter of phosphate buffered saline, PBS (0.01 M phosphate, 0.85% NaCl, pH 7.6) was prepared. To that was added 2 mg/ml Chloramine-T in PBS, in increments of 50 $\mu l$ until the potential increased to about 150 to 200 millivolts (mv) above the starting potential, keeping the pH of solution between 7.4 and 7.8. Labelling efficiency was checked every 10-15 minutes by the trichloroacetic acid (TCA) precipitation test, as follows:

To 1 ml of 0.01 M sodium metadisulfite solution was added 0.01 ml of iodinated protein solution. To this solution was added 0.5 ml of a 1/10 dilution of any normal serum. To this was added 0.5 ml of 30% TCA, mixing thoroughly, followed by centrifugation at 500 g-1000 g for two minutes. After decanting the supernatant radioactivity of both the supernatant and the precipitate were counted to determine the percentage of iodine bound to protein, in accord with the following equation:

$$\% \text{ bound} = \frac{\text{cpm precipitate}}{\text{cpm precipitate} + \text{cpm supernatent}} \times 100$$

80 to 90% efficiency was usually obtained within 30 minutes. At this time, the addition of solution containing 5 mg of sodium metabisulfite per ml. of PBS was begun, 20 microliters at a time. After lowering the potential to the starting potential or slightly above (0 to +50 above the starting potential), free $^{125}I$ can be removed from $^{125}I$-labelled CIG by dialysis or chromatography.

$^{131}I$ labelled CIG can be prepared in the same manner.

EXAMPLE 12

Localization of Radiolabelled CIG at the Site of Burned Tissue

Controlled three-centimeter full thickness burns are administered to one side of each of several rats. Each of the burned rats were injected intravenously (IV) with 100 $\mu Ci$ $^{125}I$-CIG (1 $\mu Ci/\mu g$) (Example 11) and a 10 to 20 fold increase of isotope localization in the margins of the burn is found when compared to adjacent normal tissue. The site is visualized with the aid of a gamma camera.

As a control to evaluate non-specific localization attributable to tissue fluid shifts, the distribution of $^{125}I$-albumin is also determined in the same manner as above.

A 2-3 fold increase in $^{125}I$-albumin is observed at the margins of the burn as a result of increases in vascular permeability compared to the 10 to 20 fold increase that is observed using $^{125}I$-CIG.

EXAMPLE 13

Localization of Radiolabelled CIG in Abcesses

Abcess formation is induced in the flank muscle of rats by the injection of E. coli or turpentine. The rats are injected IV with 100 $\mu Ci$ of $^{131}I$-CIG (1 $\mu Ci/\mu g$) (Example 11) and evaluated with the aid of a gamma camera. The radiolabelled CIG localized the abcess.

EXAMPLE 14

Localization of Radiolabelled CIG in Thrombi

Thrombosis of the femoral vein of a rabbit is produced by surgically inserting a balloon cuff in the vein. After healing of the surgical lesion, the cuff is inflated producing stasis and thrombosis. The rabbit is injected IV with 200 $\mu CI$ $^{125}I$-CIG (1 $\mu Ci/\mu g$) (Example 11) during early and late clot formation, resolution and encapsulation, and these phases are visualized with the aid of a gamma camera. The radiolabelled CIG localized at the site of thrombosis.

EXAMPLE 15

Localization of Radiolabelled CIG in Ulcers

Gastric ulcers are induced in rabbits by mechanical manipulating of the gastric mucosa following the insertion of a gastroscope with mucosal biopsy. The rabbits are injected IV with 200 $\mu Ci$ $^{131}I$-CIG (1 $\mu Ci/\mu g$) (Example 11) and the lesion is visualized with the aid of a gamma camera. The radiolabelled CIG localized at the ulcer site.

EXAMPLE 16

Localization of Radiolabelled CIG in Infarcts

Infarcts are induced in both rats and dogs by surgically ligating the coronary artery. The animals are injected IV with radiolabelled CIG and the infarct is visualized with a gamma camera. Rats are injected with 100 $\mu Ci$ $^{125}I$-CIG (1 $\mu Ci/\mu g$) and dogs with 1 mCi $^{131}I$-CIG(1 mCi/mg)). Histologically the infarct is not recognized until 4-6 hrs. If radiolabelled CIG is injected 1 to 3 hours after inducing an experimental infarction, it localizes in the same area as that which histologically appears to be infarcted and the localization can be visualized with the aid of a gamma camera. Localization increases over the first 6-12 hours post-infarction and clearly deposits in the damaged area. When compared with normal adjacent tissue, there is a 10 to 50-fold increase in radioactivity associated with the infarcted region.

EXAMPLE 17

Tumor Metastases

Hepatomas were produced in Buffalo rats by injecting them with the transplatable Moris Hepatoma. Tumor-bearing rats were injected IV with 100 μCi of $^{125}$I-CIG (1 μCi/μg) and the animals were imaged with the aid of a gamma camera. The radiolabelled CIG localized at the tumor site with target to nontarget ratio greater than 10 to 1.

EXAMPLE 18

Lymph node metastases are induced in dogs by lymphatic injection of histocompatible tumor. The dogs are then injected intralymphatically with 1 mCi $^{131}$I-CIG(1 mCi/mg), and lymphatic change due to metastasis is visualized with the aid of a gamma camera.

The invention has been described in detail with specific reference to the preferred embodiments thereof. However, it will be appreciated that those skilled in the art, upon reading this disclosure, may make modifications thereof within the spirit and scope of the invention.

I claim:

1. A preparation comprising affinity purified, biologically active cold insoluble globulin having a specific opsonic activity of at least 1000 units per milligram of cold insoluble globulin protein.

2. The preparation of claim 1 wherein said cold insoluble globulin is human cold insoluble globulin.

3. The preparation of claim 1 wherein said specific opsonic activity is at least 2000 units per milligram of protein.

4. The preparation of claim 3 wherein said cold insoluble globulin is human cold insoluble globulin.

5. A method for purifying cold insoluble globulin comprising:
   preparing antisera to the cold insoluble globulin to obtain anti-CIG;
   attaching said anti-CIG to a substrate to form anti-CIG-substrate;
   contacting a fluid comprising cold insoluble globulin to be purified with the anti-CIG-substrate to remove the cold insoluble globulin from the fluid;
   separating the anti-CIG-substrate with the cold insoluble globulin attached thereto from the fluid and
   eluting purified cold insoluble globulin from the anti-CIG-substrate.

6. The method according to claim 5 further comprising loading said anti-CIG-substrate into a chromatograph column.

7. The method according to claim 5 wherein said cold insoluble globulin is eluted from the anti-CIG-substrate using a solution of glycine and hydrochloric acid.

8. The method according to claim 7 wherein the eluate is neutralized.

9. A radiopharmaceutical preparation comprising a pharmaceutically acceptable carrier containing purified biologically active cold insoluble globulin having a specific opsonic activity of at least 500 units per milligram of cold insoluble globulin protein, said cold insoluble globulin being radiolabelled.

10. The radiopharmaceutical preparation according to claim 9 wherein said cold insoluble globulin is labelled with at least about one atom of radionuclide per ten molecules of cold insoluble globulin.

11. The radiopharmaceutical preparation of claim 9 wherein said cold insoluble globulin is labelled with radioactive iodine.

12. The radiopharmaceutical preparation of claim 9 wherein said cold insoluble globulin has a specific opsonic activity of at least 1000 units per milligram of protein and is labelled with at least about one atom of radioactive iodine per ten molecules of cold insoluble globulin.

13. The radiopharmaceutical preparation of claim 12 wherein said radioactive iodine is $^{125}$I or $^{131}$I.

14. The radiopharmaceutical preparation of claim 12 wherein said cold insoluble globulin is labelled with about 1.5 atoms of radioactive iodine per molecule of protein.

15. The radiopharmaceutical preparation of claim 12 wherein said specific opsonic activity is at least 2000 units per milligram of cold insoluble globulin protein.

16. The radiopharmaceutical preparation of claim 9 wherein said cold insoluble globulin is human cold insoluble globulin.

17. The radiopharmaceutical preparation of claim 16 wherein said specific opsonic activity is at least 1000 units per milligram of cold insoluble globulin protein.

18. The radiopharmaceutical preparation of claim 16 wherein said cold insoluble globulin is labelled with radioactive iodine.

19. A radiopharmaceutical preparation comprising a radiolabelled biologically active cold insoluble globulin in a pharmaceutically acceptable carrier, said radiolabelled cold insoluble globulin having been made by radiolabelling cold insoluble globulin having a specific opsonic activity of at least 1000 units per milligram of cold insoluble globulin.

20. The radiopharmaceutical preparation of claim 19 wherein said cold insoluble globulin is human cold insoluble globulin.

21. The radiopharmaceutical preparation of claim 20 wherein said specific opsonic activity is at least 2000 units per milligram of cold insoluble globulin protein.

22. The radiopharmaceutical preparation of claim 20 wherein said cold insoluble globulin is labelled with radioactive iodine.

23. A method for in vivo visualizing a site of protein or cellular components expressing CIG-binding determinants in a higher animal, said method comprising injecting said animal with a radiopharmaceutical preparation containing radiolabelled affinity purified cold insoluble globulin having a specific opsonic activity of at least 1000 units per milligram of protein, localizing the cold insoluble globulin at said site, and visualizing said site with radioscintigraphic imaging apparatus.

24. The method according to claim 23 wherein said higher animal is a human being and said cold insoluble globulin is human cold insoluble globulin.

25. A method for in vivo visualizing a site of thrombi or tissue damage in a higher animal, said method comprising injecting said animal with a radiopharmaceutical preparation containing radiolabelled cold insoluble globulin, localizing the cold insoluble globulin at said site of thrombi or tissue damage, and visualizing said site of thrombi or tissue damage with radioscintigraphic imaging apparatus.

26. A method for in vivo visualizing a burn site in a higher animal, said method comprising intravenously injecting said animal with a radiopharmaceutical preparation containing radiolabelled cold insoluble globulin, localizing the cold insoluble globulin at said burn site, and visualizing said site with radioscintigraphic imaging apparatus.

27. A method for in vivo visualizing a site of thrombi in a higher animal, said method comprising intravenously injecting said animal with a radiopharmaceutical preparation containing radiolabelled cold insoluble globulin, localizing the cold insoluble globulin at the site of said thrombi, and visualizing said site with radioscintigraphic imaging apparatus.

28. A method for in vivo visualizing a site of an ulcer in a higher animal, said method comprising intravenously injecting said animal with a radiopharmaceutical preparation containing radiolabelled cold insoluble globulin, localizing the cold insoluble globulin at said site of said ulcer, and visualizing said site with radioscintigraphic imaging apparatus.

29. A method for in vivo visualizing an infarct in a higher animal, said method comprising intravenously injecting said animal with a radiopharmaceutical preparation containing radiolabelled cold insoluble globulin, localizing the cold insoluble globulin at said infarct, and visualizing said infarct with radioscintigraphic imaging apparatus.

30. A method for in vivo visualizing a site of lymph node metastases in a higher animal, said method comprising lymphatically injecting said animal with a radiopharmaceutical preparation containing radiolabelled cold insoluble globulin, localizing the cold insoluble globulin at said site of said lymph node metastases, and visualizing said site with radioscintigraphic imaging apparatus.

31. A method for in vivo visualizing of tumors in a higher animal, said method comprising when intravenously injecting said animal with a radiopharmaceutical preparation containing radiolabelled cold insoluble globulin, localizing the cold insoluble globulin at the site of said tumor, and visualizing said tumor with radioscintigraphic imaging apparatus.

32. A preparation comprising biologically active cold insoluble globulin having a specific opsonic activity of at least 1000 units per milligram of protein.

33. A preparation according to claim 32, wherein said cold insoluble globulin is human cold insoluble globulin.

34. A preparation according to claim 32, wherein said specific opsonic activity is at least 2000 units per milligram of protein.

35. A preparation according to claim 34, wherein said cold insoluble globulin is human cold insoluble globulin.

36. A preparation in accord with any of claims 32, 33, 34 or 35, wherein said cold insoluble globulin is purified by an affinity purification method.

* * * * *